United States Patent
Kroesbergen

(10) Patent No.: US 6,946,189 B2
(45) Date of Patent: *Sep. 20, 2005

(54) SUBSTRATE WITH SUPER-ABSORBENT MATERIAL, METHOD FOR MANUFACTURE THEREOF AND USE

(75) Inventor: Aalbertus Pieter Kroesbergen, Veenendaal (NL)

(73) Assignee: Stockhausen GmbH & Co. KG, Krefeld (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/455,574

(22) Filed: Dec. 6, 1999

(65) Prior Publication Data

US 2003/0153228 A1 Aug. 14, 2003

Related U.S. Application Data

(60) Continuation of application No. 08/442,417, filed on May 16, 1995, now abandoned, which is a division of application No. 08/875,237, filed as application No. PCT/NL96/00039 on Jan. 23, 1996, now Pat. No. 5,998,312.

(30) Foreign Application Priority Data

Jan. 23, 1995 (NL) ............................................. 9500118
Jun. 15, 1995 (NL) ............................................. 1000572

(51) Int. Cl.[7] .............................................. B32B 33/00
(52) U.S. Cl. .............................. 428/304.4; 428/305.5; 428/316.6; 428/317.9; 428/378; 442/221
(58) Field of Search ............................. 429/36.9, 317.9, 429/474.9, 477.7, 522, 532, 913, 36.5, 305.5, 316.6, 319.9, 319.3, 378; 442/221, 370; 472/244, 336, 373, 487, 541

(56) References Cited

U.S. PATENT DOCUMENTS

| 4,017,653 | A | | 4/1977 | Gross |
| 4,076,663 | A | | 2/1978 | Masuda et al. ...... 260/17.4 GC |
| 4,154,898 | A | | 5/1979 | Burkholder, Jr. |
| 4,321,997 | A | * | 3/1982 | Miller |
| 4,613,543 | A | * | 9/1986 | Dabi |

(Continued)

FOREIGN PATENT DOCUMENTS

| EP | 0040087 | 11/1981 |
| EP | 0184596 | 5/1986 |
| EP | 0188959 | 7/1986 |

OTHER PUBLICATIONS

Database WPI, Section Ch. Week 8908, Derwent Publication Ltd., London, GB; AN 89–058540 XP002003530 & JP,A,01 011 675 (Nippon Shokubai Kagaku), Jan. 17, 1989.
Database WPI, Section Ch. Week 9033, Derwent Publications Ltd., London, GB; AN 90–249590 XP002003531 & JP,A,02 172 739 (Sumitomo Seika Chem), Jul. 4, 1990.

*Primary Examiner*—Jonathan Johnson
(74) *Attorney, Agent, or Firm*—The Webb Law Firm

(57) ABSTRACT

The invention relates to a substrate provided with super-absorbent material to be manufactured by allowing suitable monomers to polymerize in the presence of a catalyst in order to obtain a polymer solution, adding a cross-linking agent to the polymer solution to obtain a pasty composition, subsequently applying the composition on or in a substrate and allowing the applied composition to dry and cross-link in order to obtain the substrate with the super-absorbent material. The pasty composition further contains other additives. The invention further relates to a method for manufacturing such a substrate. The substrates can be used as sheathing material in cables, in hygiene products such as baby napkins, sanitary towels and incontinence products, in or as packagings and packaging materials and in agricultural substrates. The invention also relates to such products.

19 Claims, 1 Drawing Sheet

U.S. PATENT DOCUMENTS

| | | | |
|---|---|---|---|
| 4,747,346 A | | 5/1988 | Geel |
| 5,062,954 A | * | 11/1991 | Leedy et al. |
| 5,204,175 A | | 4/1993 | Umedg et al. |
| 5,246,770 A | | 9/1993 | Bottiglione et al. ........ 428/244 |
| 5,275,884 A | * | 1/1994 | Nishino et al. |
| 5,384,179 A | * | 1/1995 | Roe et al. .................... 428/192 |
| 5,391,161 A | * | 2/1995 | Hellgren et al. |
| 5,462,699 A | * | 10/1995 | Montgomery |
| 5,998,312 A | * | 12/1999 | Kroesbergen |

\* cited by examiner

SUBSTRATE WITH SUPER-ABSORBENT MATERIAL, METHOD FOR MANUFACTURE THEREOF AND USE

This is a con of Ser. No. 08/442,417 filed May 16, 1995, now abandoned, which is a division of U.S. patent application Ser. No. 08/875,237, filed Sep. 9, 1997 now U.S. Pat. No. 5,998,312 which is a 371 of PCT/NL96/00039 filed Jan. 23, 1996.

BACKGROUND OF THE INVENTION

1. Field of the Invention

The present invention relates to a substrate provided with a super-absorbent material, to a method for the manufacture thereof, a method for manufacturing the super-absorbent material, in addition to the use of the substrate in different products.

2. Description of the Related Art

Super-absorbent materials used for a variety of applications have existed for decades. Such super-absorbent materials are capable of binding a multiple of their own weight in liquid, particularly water, sometimes up to five hundred times as much.

The super-absorbent capacity of such materials is based on swelling. The materials are at least partially cross-linked polymer chains containing a large number of COOH groups. Through contact with water or an aqueous liquid hydrogen atoms will split off and $COO^-$ groups will be formed. These negatively charged carboxylate groups repulse each other, whereby the cross-linked polymer forms a three-dimensional network, in which the water molecules are as it were captured. The water molecules are held in the super-absorbent material by means of hydrogen bridges. The (partial) cross-linking of the material is essential for the effectiveness thereof, since "separate" polymer chains would simply dissolve in the liquid instead of absorbing it.

Super-absorbent materials occur as powders or fibers. The advantage of powders is that they have a markedly higher absorption capacity than fibers due to their significantly larger surface area. Super-absorbent fibers are moreover more expensive.

Powders are usually applied to a substrate, which in turn is further processed into the end product. In particular cases powders are also directly processed. The great drawback of powder however is that it causes dusting and dust nuisance both in the manufacture of substrates coated with powder and in the processing of those substrates or the loose powders themselves. Dust nuisance is not only very unpleasant but also causes loss of material and therefore waste and is moreover bad for the health of those working with the powders.

It is therefore the object of the present invention to provide a substrate provided with a super-absorbent material which does not have the above stated drawbacks.

SUMMARY OF THE INVENTION

This is achieved by the invention by manufacturing the substrate by causing suitable monomers to polymerize in the presence of a catalyst in order to obtain a polymer solution, adding a cross-linking agent to obtain a pasty composition, subsequently applying the composition on or in a substrate and allowing the applied composition to dry and cross-link to obtain the substrate with the super-absorbent material.

In an alternative embodiment of the invention the polymer solution can also be prepared, instead of by polymerization, by dissolving already formed polymers in water or an aqueous solvent and only then adding the cross-linking agent. The thus obtained composition can then again be applied to a suitable substrate.

DETAILED DESCRIPTION OF THE PREFERRED EMBODIMENTS

Figure 1:
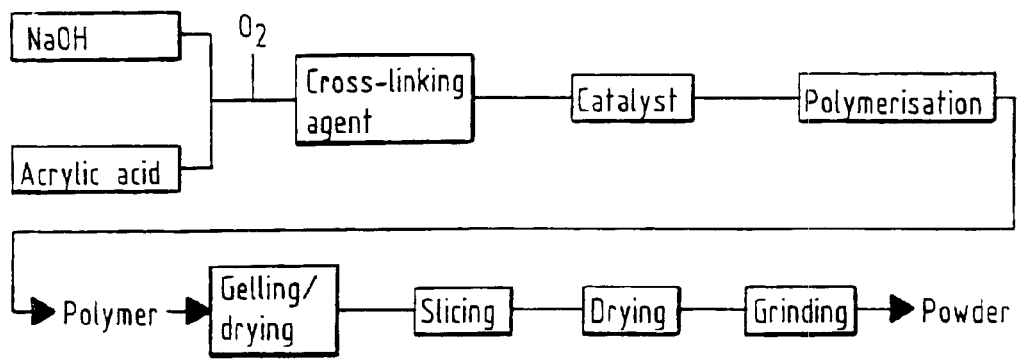
FIG. 1 shows a schematic diagram of preparatory steps for manufacturing a super-absorbent powder according to prior art.

The conventional method for preparing a super-absorbent powder consists of adding together suitable monomers and a cross-linking agent and causing these to polymerize in the presence of a catalyst. The polymer obtained in this manner is gelled and dried and subsequently ground to powder. FIG. 1 shows a schematic outline of the prepatory steps for manufacturing a super-absorbent powder according to the prior art.

Figure 2:
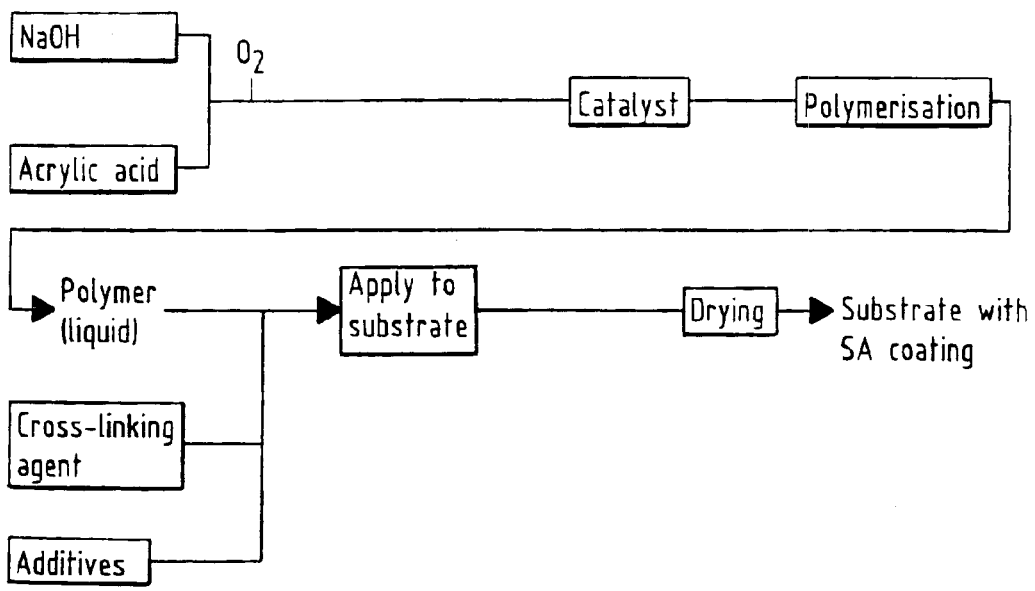
FIG. 2 shows a schematic diagram or me process of the present invention.

In the method according to the invention however, the cross-linking step is not performed during polymerization but only thereafter. Cross-linking takes place just before, during or after the application of the mixture of the polymer solution and the cross-linking agent. The material with super-absorbent properties is subsequently manufactured by drying. FIG. 2 shows the process according to the invention in diagrammatic form.

The advantage of the process sequence of the present invention is that dust nuisance no longer occurs either during applying of the super-absorbent material in or on a substrate or during processing of the substrate itself. The occurrence of additional waste is also hereby prevented.

If desired, other additives can also be introduced into the composition just before, simultaneously with or after addition of the cross-linking agent. The object of such additives is for instance to change the viscosity of the composition, whereby the application is facilitated, to improve the adhesion of the material to the substrate, to soften the super-absorbent material, whereby the adhesion is also improved, to increase the conducting properties or to cause the composition to foam either after or during the application.

Additives which change the viscosity of the composition can be chosen for instance from acrylates, polyurethane or combinations thereof. Changing the viscosity may be necessary in respect of particular methods of applying the composition to the substrate. In screen printing techniques it may be desired in particular cases for the applied quantity of material not to run out or only to run out slowly. The spreading speed can be influenced by increasing the viscosity.

Additives for improving the adhesion of the super-absorbent material to the substrate are for instance polyamides (PA), polyethylene (PE), ethylene vinyl acetate (EVA) or combinations thereof. These materials adhere relatively well to the commonly used substrates. By including them in the super-absorbent material the adhesion thereof can be improved. Such adhesive agents can also be arranged as coating layer on the substrate prior to application of the pasty composition. The adhesion can also be enhanced by adding plasticizers. Suitable plasticizers are preferably plasticizers which are co-polymerized with the super-absorbent material so that they cannot diffuse from the polymer into for instance cable insulation. Plasticizers ensure that the resulting super-absorbent material does not become too hard, whereby it could easily detach from the substrate.

To improve the conductivity of the material or end product, for instance soot (carbon) or other conducting materials can be mixed in.

Suitable foaming agents are for instance Servo Amfolyt JA 140™, Nekanil™ or combinations thereof. The advantage of an absorbent material in the form of a foam is that the surface is significantly enlarged. Hereby the swelling capacity likewise increases because the water molecules have easier access to the carboxyl groups of the polymer network and these can thereby hydrolyse more rapidly.

In principle any polymer with suitable swelling properties can be processed in the manner outlined above to a pasty composition which can be applied to a substrate. Particularly recommended however are polyacrylates, preferably sodium- or ammonium-neutralized acrylamides and cellulose-like polymers. A suitable cross-linking agent is added depending on the polymer. The skilled person in this field using his average professional knowledge will be capable of selecting suitable cross-linking agents.

In principle any desired material can be used as substrate as long as adhesion of the super-absorbent material thereto is possible. Examples of substrates are for instance fabrics, non-wovens, paper, films, for instance of plastic or metal, tape material, for instance of aluminum, or also petrojelly-like filling compounds. In addition to flat substrates filamentary or fibrous substrates can also be used.

The present invention further relates to a method for manufacturing a substrate provided with a coating of super-absorbent material, comprising of allowing suitable monomers to polymerize in the presence of a catalyst, adding a cross-linking agent thereto in order to obtain a pasty composition, subsequently applying the composition to a substrate and allowing the applied composition to cross-link and dry to obtain the substrate with the super-absorbent material.

According to an alternative embodiment the polymer solution can here also be manufactured, instead of by polymerization, by dissolving polymer chains in water or an aqueous solvent.

There are different possibilities for applying the pasty composition to the substrate. Full surface coating results in a substantially closed layer. In principle a closed layer has a relatively low absorption capacity. For particular applications, however, such a product may be desired. In addition to surface coating, the pasty material can however also be applied by means of brushing, rolling and the like.

A third method of application is impregnation. Impregnation takes place for instance by transporting the substrate together with the pasty composition through two rollers. Depending on the wettability of the substrate, a closed layer results or accumulations of the composition form locally. The latter occurs particularly when a hydrophobic substrate is used.

A third possibility of applying the pasty composition is by means of screen printing techniques. The material is herein applied to the substrate through a template. The form, distribution and dimensions of the openings in the template determine the resulting pattern on the substrate.

The properties of the swelling material depend on a number of factors. Thus both the ratio between temperature (during application and drying) and the drying time as well as the viscosity of the composition are important for the adhesion to the substrate and for the swelling capacity. Cross-linking agents are generally active at relatively high temperatures and in aqueous environments. In the ideal case, the cross-linking should take place at between 150 and 200° C., preferably about 175° C., and at a pressure such that water has not yet evaporated. In practice however, atmospheric pressure and a temperature of about 175° C. are often chosen. It has been found according to the invention that with a drying time of between 1 and 3 minutes at 175° C. an absorbent material with good properties is obtained. The time and temperature can however vary depending on the ratio between the quantities of acrylate and cross-linking agent and the viscosity of the mixture.

It has been found that in the first drying run the evaporation of the cross-linking agent must be prevented as far as possible. This can be achieved by operating with the lowest possible air circulation.

In addition, the form in which the super-absorbent material is applied is also important for the absorption properties. With powders it has been found in practice that particles with a diameter of between about 100 and 200$\mu$ have the best absorption properties. According to the invention the composition is therefore preferably applied in the form of discrete, substantially semi-spherical islets with a diameter of between about 100 and 200$\mu$. Depending on the application the islets may however also have greater or smaller diameters, for instance between 10 and 1000$\mu$, preferably between 50 and 500$\mu$.

The distribution of the islets on the substrate can be random or in accordance with a determined pattern. In addition, a greater number of islets or islets with a different diameter may be arranged at determined locations on the substrate in order to locally increase the absorption capacity. This is important for instance when the product is used in hygiene products such as baby napkins and sanitary towels. A skilled person will be able to ascertain by means of simple tests which pattern is most suitable for a particular application.

The absorption capacity of the substrate depends on the quantity of super-absorbent material applied. In the present case 30 g per $m^2$ would already provide sufficient absorption. Starting from this given information, it can be calculated how much material must applied per islet of 200$\mu$ and what the distance between the islets must be, for instance by means of the following calculation:

the volume of an islet is:

$$\tfrac{2}{3}\pi r^3 = \tfrac{2}{3} * 3.14 * (0.002)^3 = 1.7 \cdot 10^{-8} \text{ dm}^3$$

the specific weight is set at:
1 kg/$m^3$
the weight of one semi-sphere is then:
$1.7 \cdot 10^{-5}$ g
a weight of 30 g/$m^3$ then results in:
$1.75 \cdot 10^6$ semi-spheres
the diameter surface of one semi-sphere is:
$3.14 \cdot 10^{-8}$ $m^2$
the total surface of the dots together is:
0.0553 $m^2$
the distance between the dots amounts to:

$$8 \cdot 10^{-6} - 2 \cdot 10^{-6} = 600\mu$$

The quantity of material to be applied is determined by the form and dimensions of the openings in a template. In the case of semi-spherical islets the material will preferably be applied in the shape of a cylinder and will then assume the ideal semi-spherical shape by flowing out slightly.

It has been found that super-absorbent material applied with a CP30 template has a swelling capacity of about 1 mm per 10 g/m² in tap water. A full surface coated layer of absorbent material has for instance a swelling capacity of about 0.2 mm per 10 g/m² (in tap water with an average conductivity).

The substrate with the super-absorbent material according to the invention can in principle be used in any field in which at the moment super-absorbent powders and fibers and substrate materials provided with super-absorbent powders and fibers are also used.

An example of a particularly advantageous application is the use of the substrate as sheathing material in the cable industry. Sheathing material is used for electricity cables and data cables and has a number of functions. It serves for instance to embed the conducting part of the cable and to form a barrier to the environment (the so-called bedding function). In addition, sheathing material is used to hold together the components of a cable (so-called binding). Furthermore, determined components of a cable must be mutually separated (separation). Sheathing material is also used for this purpose. An important fourth and final function is so-called water-blocking, which must prevent water penetrating to the core in transverse as well as longitudinal direction. The sheathing material according to the invention is particularly suitable for this latter function. Heretofore petrojelly-like compounds or substrate materials coated with a super-absorbent powder have been used for this purpose. Processing of petrojellies is far from agreeable and causes a considerable degree of smearing, leakage of the jellies etc. during manufacture of the cables as well as during connection thereof. The drawbacks of powdery super-absorbent materials are already described above. The substrate according to the invention is particularly suitable as water-blocking material in cables.

Super-absorbent materials are in addition also much used in hygiene products such as baby napkins, sanitary towels and incontinence products. In the manufacture of such products and the use thereof the drawbacks of the powders used heretofore are prevented by using a substrate according to the invention.

Another application of the substrate according to the invention lies in the field of agriculture, where moisture-regulating conditions can be provided, for instance in agricultural substrates, by means of the super-absorbent properties of the material.

The material can also be used in the packaging industry. In products which must be stored absolutely moisture-free, bags of silica gel are often co-packed. The invention enables packaging of the product for instance directly in a substrate provided with a super-absorbent material.

In the present application the following terminology is used. By "polymer solution" is understood a polymer-containing liquid phase before addition of a cross-linking agent. By "composition" is understood the polymer solution after addition of the cross-linking agent, prior to as well as after the application thereof to a substrate, optionally after cross-linking but still before drying. "Absorbent material" designates the composition after cross-linking and drying.

The invention will be further elucidated on the basis of the accompanying example, which is only given however by way of illustration and is not intended to limit the invention in any way whatsoever.

EXAMPLE

The super-absorbent composition according to the invention was prepared from two components. Component 1 consists of an aqueous solution of a pre-cross-linked poly(meth)acrylic acid, which can be partially present in the form of a salt. The counter-ions can in that case be sodium, potassium or ammonium. In addition, the solution can optionally contain acrylamide as co-monomer. The monomer containing the carboxyl group ((meth)acrylic acid) must however always be present in excess.

The second component is the actual reactive cross-linking agent, which preferably contains two functional groups which are capable after thermal excitation of reacting in a short time with carboxylate or carbonic acid functional groups.

Shortly before application of the mixture to the substrate, component 2 in a quantity of 0.1–5% by weight, preferably 0.5–3% by weight related to the total quantity of component 1, is added to component 1 (95–99.9% by weight) and mixed homogeneously therewith.

The mixture is applied to a suitable substrate by means of screen printing techniques with a screen having a mesh width of 500–1000, preferably 745$\mu$ in order to obtain a regular pattern of islets with a diameter of 100–500, preferably 250$\mu$ and an open area of 5–20, preferably 13%. After printing, the substrate with the mixture thereon is dried in order to cause the cross-linking process to take place. The thus obtained product has a swelling capacity of 1 mm at an application of 9 g/m² (dry).

The present invention provides a new substrate which is provided with a super-absorbent material and which during manufacturing and processing displays none of the drawbacks of the substrates coated with conventionally used super-absorbent powders. A new method is further provided for manufacturing the substrate and for the preparation. The substrate can take different forms and be used for a large number of applications.

What is claimed is:

1. A substrate comprising a super-absorbent material applied to the substrate, wherein the super-absorbent material is obtained by allowing suitable monomers to polymerize in the presence of a catalyst in order to obtain a pre-cross-linked polymer solution, adding a cross-linking agent containing two functional groups which are capable after thermal excitation of reacting within at least ten minutes with carboxylate or carbonic acid functional groups to the polymer solution to obtain a pasty composition, subsequently applying the composition on or in the substrate and allowing the applied composition to dry for one to three minutes at between 150° C. and 200° C. to form a swellable paste, and wherein the pasty composition is applied to the substrate in the form of discrete, substantially semi-spherical islets having a diameter of 10 $\mu$ to 1000$\mu$.

2. A substrate comprising a super-absorbent material applied to the substrate, wherein the material has a significantly enlarged surface area achieved by having the super-absorbent material in the form of a plurality of discrete, substantially semi-spherical islets with a diameter between 10 and 100$\mu$.

3. The substrate as claimed in claim 1, wherein the super-absorbent material is a foam.

4. The substrate as claimed in claim 1, wherein the pasty composition applied to the substrate is allowed to dry and cross-link.

5. The substrate as claimed in claim 4, further comprising adding a foaming agent to the pasty composition prior to applying the composition to the substrate, wherein the composition is caused to foam at any time after addition of the foaming agent.

6. The substrate as claimed in claim 5, wherein the pasty composition further comprises at least one other additive chosen from agents for changing the viscosity of the composition, agents for improving the adhesion of the super-absorbent material to the substrate, agents for softening the super-absorbent material, and agents for making the composition conductive.

7. The substrate as claimed in claim 6, wherein the agents for changing the viscosity of the composition are acrylates, polyurethane or combinations thereof.

8. The substrate as claimed in claim 6, wherein the agents for improving the adhesion of the super-absorbent material to the substrate are polyamide, polyethylene, ethylene vinyl acetate or combinations thereof.

9. The substrate as claimed in claim 6, wherein the agents for softening the super-absorbent material are plasticizers which co-polymerize in the polymer.

10. The substrate as claimed in claim 1, wherein the cross-linking agent contains two functional groups which are capable after thermal excitation of reacting in a short time with carboxylate or carbonic acid functional groups.

11. The substrate as claimed in claim 1, wherein the composition comprises soot to make the composition conductive.

12. The substrate as claimed in claim 1, wherein the super-absorbent material is obtainable by preparing a polymer solution by dissolving a polymer in an aqueous solvent, adding a cross-linking agent to the polymer solution to obtain a pasty composition, and applying the composition to the substrate.

13. The substrate as claimed in claim 1, wherein the super-absorbent material is selected from the group consisting of a cross-linked polyacrylate, a polyamide, or a combination thereof.

14. The substrate as claimed in claim 1, wherein the substrate is one of a fabric, a non-woven, a paper, a film, aluminum tape, or a fiber.

15. The substrate as claimed in claim 1, wherein the pasty composition consists of 95–99.9% by weight of an aqueous solution of pre-cross-linked poly(meth)acrylic acid and 0.1–5% by weight of a cross-linking agent.

16. A cable comprising a sheathing material which is formed from the substrate as claimed in claim 1.

17. A hygiene product selected from the group consisting of a baby napkin, a sanitary towel, and an incontinence product, comprising the substrate as claimed in claim 1.

18. A packaging material comprising the substrate as claimed in claim 1.

19. An agricultural substrate comprising the substrate as claimed in claim 1.

* * * * *

UNITED STATES PATENT AND TRADEMARK OFFICE
CERTIFICATE OF CORRECTION

PATENT NO. : 6,946,189 B2
DATED : September 20, 2005
INVENTOR(S) : Kroesbergen

It is certified that error appears in the above-identified patent and that said Letters Patent is hereby corrected as shown below:

Column 2,
Line 11, "diagram or me process" should read -- diagram of the process --.

Column 6,
Line 55, "10 and 100$\mu$" should read -- 10 and 1000$\mu$. --

Signed and Sealed this

Seventh Day of March, 2006

JON W. DUDAS
*Director of the United States Patent and Trademark Office*